United States Patent
Walsh et al.

(10) Patent No.: US 7,160,537 B2
(45) Date of Patent: Jan. 9, 2007

(54) METHOD FOR PREPARING RADIOLABELED THYMIDINE HAVING LOW CHROMOPHORIC BYPRODUCTS

(75) Inventors: Joseph C. Walsh, Pacific Palisades, CA (US); Henry C. Padgett, Hermosa Beach, CA (US); Tanea Ysaguirre, Los Angeles, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 234 days.

(21) Appl. No.: 10/736,087

(22) Filed: Dec. 15, 2003

(65) Prior Publication Data

US 2005/0131223 A1    Jun. 16, 2005

(51) Int. Cl.
*A61K 51/00* (2006.01)
*A61M 36/14* (2006.01)

(52) U.S. Cl. .................. 424/1.89; 424/1.11; 424/1.65; 424/1.81

(58) Field of Classification Search .............. 424/1.11, 424/1.65, 1.81, 1.85, 1.89, 9.1; 544/224, 544/242, 245, 253, 254; 549/200
See application file for complete search history.

(56) References Cited

U.S. PATENT DOCUMENTS

| | | | |
|---|---|---|---|
| 3,894,000 A | 7/1975 | Wechter et al. |
| 4,425,335 A | 1/1984 | Fujii et al. |
| 4,490,366 A | 12/1984 | Fujii et al. |
| 4,503,045 A | 3/1985 | Fujii et al. |
| 4,599,404 A | 7/1986 | Fujii et al. |
| 4,681,933 A | 7/1987 | Chu et al. |
| 4,757,139 A | 7/1988 | Kawaguchi et al. |
| 4,886,877 A | 12/1989 | Fujii et al. |
| 4,904,770 A | 2/1990 | Starrett, Jr. et al. |
| 4,908,440 A | 3/1990 | Sterzycki et al. |
| 4,910,300 A | 3/1990 | Urdea et al. |
| 4,921,950 A | 5/1990 | Wilson |
| 4,937,329 A | 6/1990 | Reese |
| 5,013,828 A | 5/1991 | Kikuchi et al. |
| 5,070,078 A | 12/1991 | Selway et al. |
| 5,093,232 A | 3/1992 | Urdea et al. |
| 5,101,023 A | 3/1992 | Czernecki et al. |
| 5,126,506 A | 6/1992 | Sterzycki et al. |
| 5,179,200 A | 1/1993 | Molko et al. |
| 5,190,926 A | 3/1993 | Chu et al. |
| 5,204,456 A | 4/1993 | Molko et al. |
| 5,212,293 A | 5/1993 | Green et al. |
| 5,218,106 A | 6/1993 | Sterzycki et al. |
| 5,359,053 A | 10/1994 | Rogers et al. |
| 5,428,148 A | 6/1995 | Reddy et al. |
| 5,466,787 A | 11/1995 | Chen et al. |
| 5,530,110 A | 6/1996 | Sowers |
| 5,608,048 A | 3/1997 | Gandhi et al. |
| 5,608,049 A | 3/1997 | Spector et al. |
| 5,646,269 A | 7/1997 | Matteucci et al. |
| 5,672,698 A | 9/1997 | Chen et al. |
| 5,679,785 A | 10/1997 | Engels et al. |
| 5,717,086 A | 2/1998 | Chambers et al. |
| 5,760,208 A | 6/1998 | Abushanab et al. |
| 5,932,719 A | 8/1999 | Abushanab et al. |
| 6,060,592 A | 5/2000 | Acevedo et al. |
| 6,121,438 A | 9/2000 | Abushanab et al. |
| 6,326,491 B1 | 12/2001 | Abushanab et al. |
| 6,362,329 B1 | 3/2002 | Abushanab et al. |
| 6,369,040 B1 | 4/2002 | Acevedo et al. |
| 2003/0004331 A1 | 1/2003 | Komatsu et al. |
| 2003/0087873 A1 | 5/2003 | Stuyver et al. |
| 2005/0048601 A1 | 3/2005 | Dellinger et al. |

OTHER PUBLICATIONS

Balagopala et al., "An Improved Synthesis of Azidothymidine," *Nucleosides & Nucleotides*, 15(4), pp. 899-906, 1996.
Varagnolo et al., "$^{18}$F-labeled Radiopharmaceuticals for PET in Oncology, Excluding FDG," *Nuclear Medicine & Biology*, vol. 27, pp. 103-112, 2000.
Martin et al., "A new precursor for the radiosynthesis of [$^{18}$F]FLT," *Nuclear Medicine & Biology*, 29, pp. 263-273, 2002.
Grierson et al., "Radiosynthesis of 3'-Deoxy-3'-[$^{18}$F]fluorothymidine: [$^{18}$F]FLT for Imaging of Cellular Proliferation *in Vivo*," *Nuclear Medicine & Biology*, vol. 27, pp. 143-156, 2000.
Yun et al., "High radiochemical yield synthesis of 3'-deoxy-3'-[$^{18}$F]fluorothymidine using (5'-O-dimethoxytrityl-2'-deoxy-3'-O-nosyl-β-D-*threo* pentofuranosyl)thymine and its 3-N-BOC-protected analogue as a labeling precursor," *Nuclear Medicine & Biology*, 30, pp. 151-157, 2003.
Shields et al., "Imaging Proliferation *in vivo* with [F-18]FLT and positron emission tomography" *Nature Medicine*, vol. 4, No. 11, pp. 1334-1336, Nov. 1998.
Blocher et al., "Synthesis and labeling of 5'-O-(4,4'-dimethoxytrityl)-2,3'-anhydrothymidine for [$^{18}$F]FLT preparation," *Journal of Radioanalytical and Nuclear Chemistry*, vol. 251, No. 1, pp. 55-58, 2002.
Machulla et al., "Simplified labeling approach for synthesizing 3'-deoxy-3'-[$^{18}$F]fluorothymidine ([$^{18}$F]FLT)," *Journal of Radioanalytical and Nuclear Chemistry*, vol. 243, No. 3, pp. 843-846, 2000.
Wodarski et al., "Synthesis of 3'-Deoxy-3'-[$^{18}$F]Fluoro-Thymidine with 2,3'-Anhydro-5'-O-(4,4'-Dimetheoxytrityl)-Thymidine," *Journal of Labelled Compounds and Radiopharmaceuticals*, 43, pp. 1211-1218, 2000.
Vesselle et al., "*In Vivo* Validation of 3'deoxy-3'-[$^{18}$F]fluorothymidine ([$^{18}$F]FLT) as a Proliferation Imaging Tracer in Humans: Correlation of [$^{18}$F]FLT Uptake by Positron Emission Tomography with Ki-67 Immunohistochemistry and Flow Cytometry in Human Lung Tumors," *Clinical Cancer Research*, vol. 8, 3315-3323, Nov. 2002.

*Primary Examiner*—Dameron L. Jones

(57) ABSTRACT

The invention is a method and related precursor for preparing $^{18}$F-FLT. The precursor has a butoxycarbonyl protecting group at the 5'-position that results in low amounts of chromophoric byproducts being formed during deprotection. The method for preparing $^{18}$F-FLT is efficient and makes the final purification step less complicated.

8 Claims, 2 Drawing Sheets

METHOD FOR PREPARING RADIOLABELED THYMIDINE HAVING LOW CHROMOPHORIC BYPRODUCTS

BACKGROUND OF THE INVENTION

Positron emission tomography (PET) is a diagnostic imaging technique for measuring the metabolic activity of cells in the human body. PET can show images of blood flow, glucose metabolism in the brain, or rapid changes in activity in various areas of the body. It can be used to show changes in physiology before any change in gross anatomy has occurred. PET has been used in diagnosing diseases such as cancer, heart disease, Alzheimer's disease, Parkinson's disease, and schizophrenia.

PET uses chemical compounds that are labeled with radioactive atoms that decay by emitting positrons. The most commonly used PET radioisotopes are $^{11}C$, $^{13}N$, $^{15}O$, and $^{18}F$. Typically, the labeled compound is a natural substrate, substrate analog, or drug that is labeled with a radioisotope without altering the compound's chemical or biological properties. After injection into the tissue, the radiolabeled compound should follow the normal metabolic pathway of its unlabeled counterpart. The labeled compound emits positrons as it moves through the tissue. Collisions between the positrons and electrons that are present in the tissue emit gamma rays that are detectable by a PET scanner.

Radiolabeled thymidine is a PET tracer that is useful for imaging tumors. In particular, 3'-Deoxy-3'-[$^{18}F$]-fluoro-thymidine ($^{18}F$-FLT) has been used for visualizing DNA replication in humans and animals. $^{18}F$-FLT is incorporated into DNA during the synthesis phase of the cell cycle and therefore is a useful indicator of cellular proliferation.

After injection into a patient, $^{18}F$-FLT is taken up by cells and undergoes phosphorylation by thymidine kinase-1 (TK), an enzyme that is expressed during cellular DNA synthesis. The phosphorylated FLT molecule is retained within the cell, which results in its accumulation. As a result, $^{18}F$-FLT provides insight into cellular activity and is an excellent proliferation marker for PET tumor studies.

The usefulness of $^{18}F$-FLT as a tumor imaging agent has resulted in a need to develop methods for its quick and efficient synthesis. Typical methods for preparing $^{18}F$-FLT have low reaction yields. Newer methods that increase yield require more synthetic transformations. Often, these newer methods result in chromophoric byproducts that are produced during the synthesis. For instance, dimethoxy trityl (DMT) is a protecting group that is often used to protect the 5'-hydroxy. During deprotection, DMT-OH and DMT cation are generated. DMT cation has an orange color. The formation of DMT cation is a typical example of chromophoric byproducts that can be produced during the deprotection step.

The presence of chromophoric byproducts complicates the purification process and makes it more difficult and expensive to efficiently produce $^{18}F$-FLT. During purification, the radiolabeled product is typically loaded onto a reverse phase column and eluted. If there is a large amount of byproducts, the byproducts can bleed into the final product producing an impure final product.

BRIEF SUMMARY OF THE INVENTION

The invention is a method for preparing radiolabeled nucleosides, and in particular, $^{18}F$-FLT and related precursors. The method allows the synthesis in a short number of steps with high yield.

The invention uses an $^{18}F$-FLT precursor that produces low amounts of chromophoric byproducts during the deprotection step. It has been discovered that using a t-butoxycarbonyl protecting group at the 5'-position provides several advantages. Using t-butoxycarbonyl at the 5'-position results in the formation of less chromophoric byproducts during the deprotection step. During deprotection, t-butoxycarbonyl can be converted into t-BuOH and $CO_2$. Both t-BuOH and $CO_2$ are colorless and volatile. As a result, the amount of byproducts that are generated is decreased. Thus, the invention provides a method and precursor that produce $^{18}F$-FLT in high yield with a purification process that is less complicated and more efficient.

The precursor has the following formula:

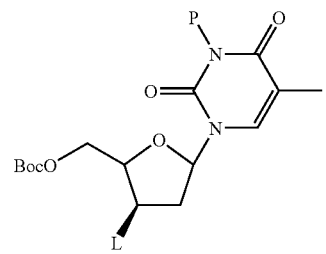

wherein P is an amine protecting group and L is a leaving group.

The preparation of $^{18}F$-FLT can begin by converting thymidine into 2,3'-anhydrothymidine. The 2,3' anhydro ring is opened to produce 3'-beta hydroxyl thymidine. In the next steps, the 5'-hydroxyl group is protected, the 3'-hydroxy group is converted into a leaving group, and the 3-N amine is protected with an amine protecting group.

The precursor is immediately ready for radiolabeling or alternatively can be stored for future use. After radiolabeling, the protecting groups are removed. Typically, the removal is carried out with acid hydrolysis.

BRIEF DESCRIPTION OF THE SEVERAL VIEWS OF THE DRAWING(S)

Having thus described the invention in general terms, reference will now be made to the accompanying drawings wherein:

The invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements.

DETAILED DESCRIPTION OF THE INVENTION

The synthesis of radiolabeled nucleosides can begin with a nucleoside having a pyrimidine base, such as thymidine, uridine, or cytidine. In the invention the nucleoside with a pyrimidine base is converted into an anhydronucleoside.

Figure 1:
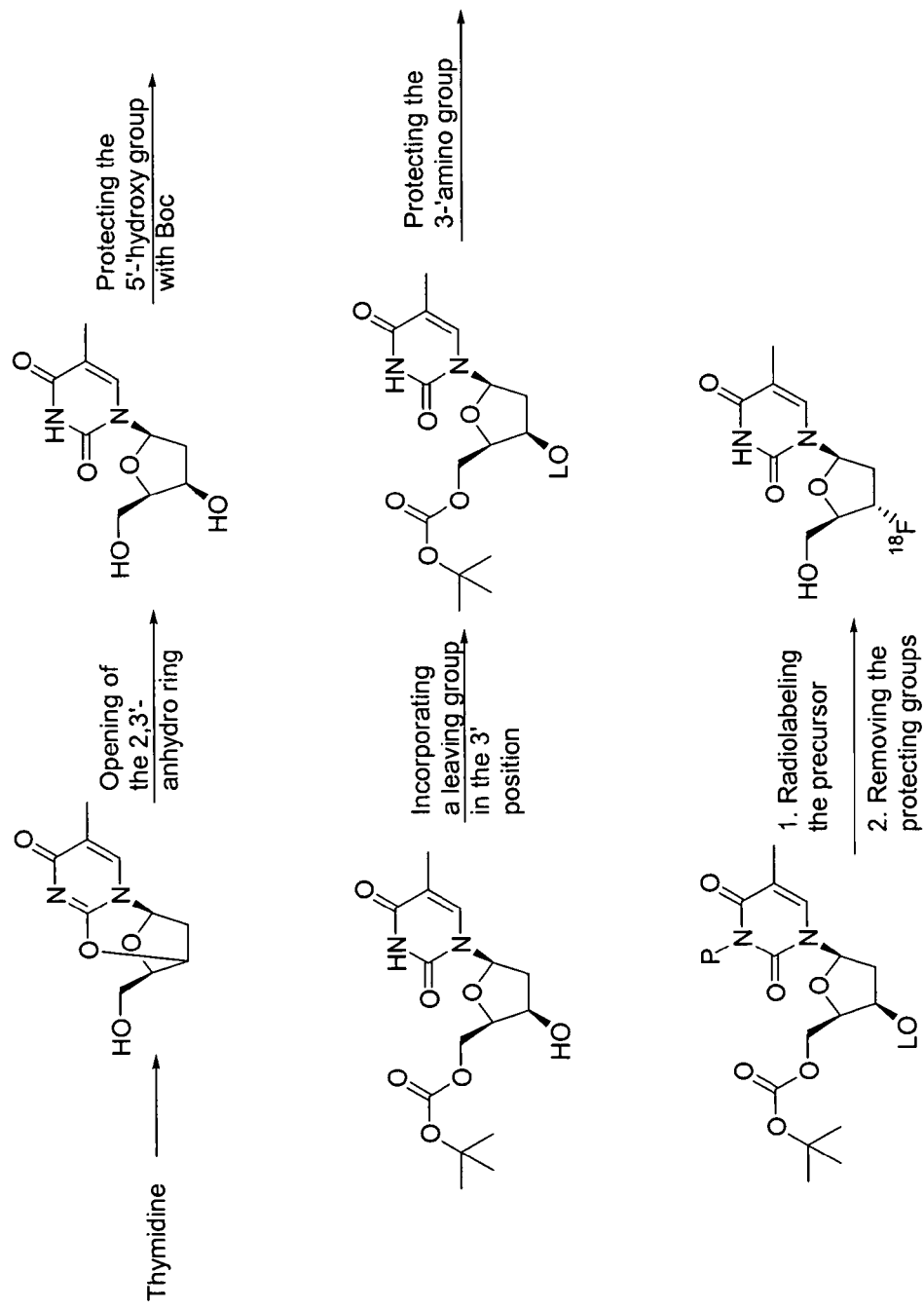
FIG. 1 illustrates a reaction scheme for preparing $^{18}F$-FLT.
Figure 2:
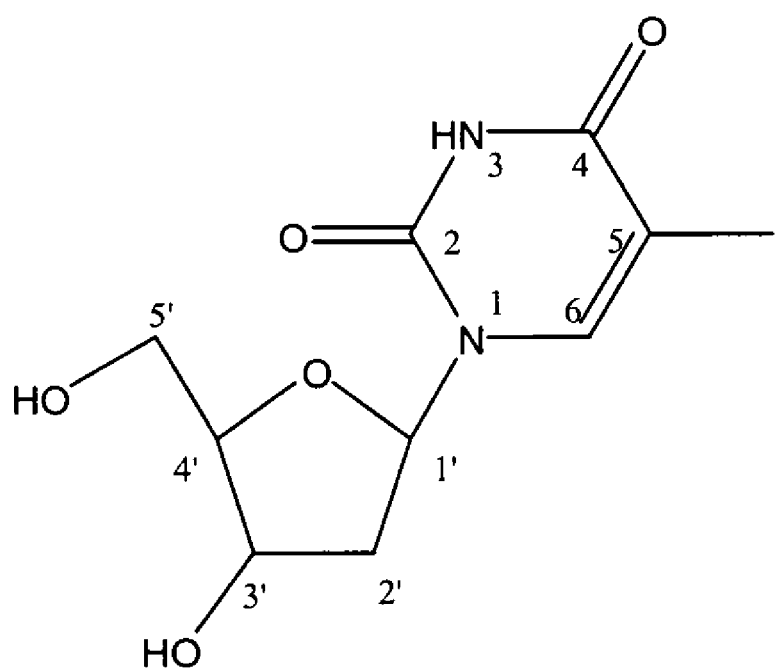
FIG. 2 is structural drawing of thymidine showing the numbering of carbon atoms in the compound.

FIG. 1 illustrates an exemplary reaction scheme for preparing $^{18}$F-FLT in accordance with the invention. For ease of discussion, FIG. 2, illustrates a thymidine molecule in which the carbon atoms have been numbered. The numbering convention shown in FIG. 2 is used throughout the disclosure. It should be recognized that the carbon atoms could be numbered differently and that the invention is not limited by any particular numbering format.

The synthesis of $^{18}$F-FLT and its related precursor can begin with thymidine. As illustrated in FIG. 1, the method of preparing $^{18}$F-FLT contains the following steps outlined below:
  a. converting thymidine into 2,3'-anhydrothymidine;
  b. opening the 2,3'-anhydro ring;
  c. protecting the 5'-hydroxyl group with t-butoxycarbonyl (boc);
  d. incorporating a leaving group at the 3'-position;
  e. protecting the 3-N amine group;
  f. radiolabeling the $^{18}$F-FLT precursor; and
  g. removing the amine protecting group and boc at the 5'-position.

Depending upon reaction conditions, the order of steps c, d, and e can be varied, although not necessarily with equivalent results. Each step is discussed in greater detail below.

In the first step, thymidine is converted into 2,3'-anhydrothymidine to produce a compound having the following formula:

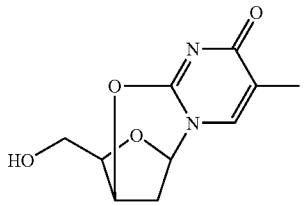

2,3'-anhydrothymidine can be a useful starting compound because it places the 3'-hydroxyl group in the beta position so that a leaving group can also be positioned in the beta position in a subsequent reaction. As a result, when fluorinated, $^{18}$F can attack the 3'-carbon anti to the leaving group and can be attached to the 3'-carbon in the α orientation.

There are a variety of known techniques for converting a nucleoside into an anhydronucleoside. For example, the anhydronucleoside can be prepared by mixing thymidine with triphenylphosphine and azeotropically drying with portions of acetonitrile (MeCN). The resulting mass is suspended in MeCN and then cooled. The mixture is rapidly stirred and diisopropylazodicarcobxylate in MeCN is added dropwise to the mixture. The resulting mixture is treated with water to form a suspension that is filtered to afford anhydrothymidine. (Grierson, J. R., Shields, A. F., *Nuclear Medicine and Biology*, 2000, 27 143–156; Balagopala, M. I., Ollapally, A. P., and Lee, H. J., *Nucleosides-Nucleotides*, 1996, 15(4) 899–906).

U.S. Pat. No. 5,717,086 discloses a method of converting a nucleoside into a 2,3'-anhydronucleoside by reacting it with a dehydrating agent in the presence of an acid. Specifically, it discloses that 2'-deoxyuridine may be reacted with a combination of diisopropylazodicarboxylate or diethylazodicarboxylate and a triaryl- or trialkyl-phosphine or -phosphite, e.g., triphenylphosphine, preferably in the presence of an acid, in an inert polar solvent. It should be recognized that there are many different methods that can be used to convert a nucleoside into its anhydronucleoside derivative, although not necessarily with equivalent results.

Alternatively, the synthesis may begin with a commercially available 2,3'-anhydro nucleoside, such as 2,3'-anhydrothymidine or one of its derivatives. It should be recognized that the invention can also include nucleoside derivatives that contain additional substituents provided that the substituents are non-interfering and do not prevent, block, or negatively impact the reactivity or functionality of the precursor, any reaction steps, or the final product. Such derivatives are known in the art and include, without limitation, deuterated derivatives, such as 2'-deuterated nucleosides, or derivatives having different substituents at the 5-position, such as bromomethyl, benzyl, or the like.

After converting thymidine into 2,3'-anhydrothymidine, the 2,3'-anhydro ring is opened to produce 3'-beta-hydroxyl thymidine. Typically, the ring is opened using a basic reagent such as NaOH, KOH, LiOH, alkylammonium hydroxides such as tetrabutylammonium hydroxide, and resins such as Amberlite IRA 400 (OH–).

In the next step, the 5'-hydroxy is protected with a protecting group to produce a compound having the following formula:

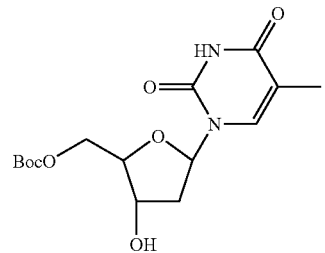

It has been discovered that protecting the 5'-hydroxyl with t-butoxycarbonyl results in the formation of fewer chromophoric byproducts during deprotection. As a result, yield is higher and the purification process is easier and more efficient.

In an alternative embodiment, the 5'-hydroxyl can be protected with protecting groups other than t-butoxycarbonyl to produce the following intermediate:

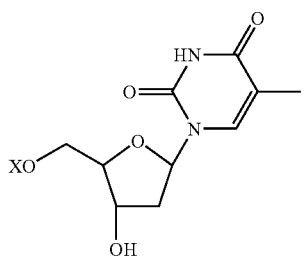

wherein X is a hydroxyl protecting group. Typically, suitable protecting groups should not contain extensive conjugation and should decompose into compounds that are volatile and colorless. Useful protecting groups include carbonates, such as methyl, methoxymethyl ethyl, and isobutyl; cyclic ethers, such as tetrahydropyranyl ether and tetrahydrafuranyl ether; and alkyl ethers, such as methoxymethyl ether, bis-(2-chloroethoxy)methyl ether, 1-ethoxyethyl ether, and 1-methyl-1-methoxyethyl ether.

A leaving group is incorporated at the 3'-position to produce the precursor having the following formula:

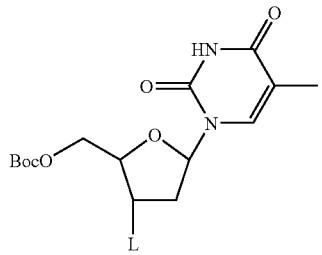

wherein L is a leaving group.

The leaving group activates the thymidine derivative and is replaced during the [$^{18}$F] fluorination step. During the radiolabeling step, [$^{18}$F] fluoride attacks the 3'-carbon atom anti to the 3'-leaving group resulting in substitution of the leaving group by a bimolecular nucleophile substitution mechanism ($S_N2$).

Leaving groups that are useful in the invention are moieties that can be displaced from the 3'-carbon atom by nucleophilic substitution. The leaving group should attach to the 3'-hydroxyl or replace it to form a leaving group at the 3'-postion. The leaving group moiety should not react with other sites or functional groups that may be present on the thymidine derivative. The leaving group should also be able to be quickly replaced by the radioisotope during the radiolabeling step. Typically, the leaving group should be replaced by [$^{18}$F]fluoride in polar aprotic solvent.

The term leaving group ("L") refers to moieties that should be susceptible to displacement by a nucleophile, wherein the 3'-hydroxy can attach to another substituent directly to form a leaving group or the 3'hydroxy may be removed in order to incorporate the leaving group. Sulfonate ester is an exemplary leaving group that is formed from a sulfonyl moiety attaching directly to the 3'-hydroxy.

Useful leaving groups that combine with the 3'-hydroxy include, without limitation, sulfonyl moieties, such as alkylsulfonyl, substituted alkylsulfonyl, arylsulfonyl, substituted arylsulfonyl, hetercyclosulfonyl or trichlorcacetimidate groups. Particularly useful groups include, without limitation, benzenesulfonyl, methylsulfonyl (mesylate), p-methylbenzenesulfonyl (tosylate), 4-nitrobenzene sulfonyl (nosylate), p-bromobenzenesulfonyl, trifluoromethylsulfonyl (triflate), trichloroacetimidate, 2,2,2-trifluoroethanesulfonyl, and imidazolesulfonyl. It should be recognized that other moieties can be used to form —O-L' leaving groups, although not necessarily with equivalent results.

Other useful $^{18}$F-FLT precursors include thymidine derivatives wherein the 3'hydroxy has been completely replaced with an alternative leaving group, such as a halogen.

The 3-N amine group is protected with an amine protecting group to produce an $^{18}$F-FLT precursor having the following formula:

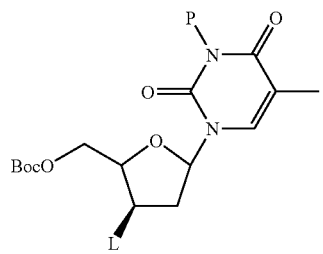

wherein P is an amine protecting group and L is the same as defined above.

Amine protecting groups that are useful in the invention should possess low chromophoric activity, prevent unwanted reactions towards the amine group, are not affected by reaction conditions, do not interfere with reactions on other portions of the molecule, and are easily removed at the end of the reaction scheme or at any other time that is appropriate. It is also desirable that the protecting group will help enhance reactions by increasing yield or selectivity.

Useful amine protecting groups include, without limitation, carbamates, such as tert-butoxycarbamate, isopropyl carbamate, pivaloyloxymethyl carbamate, and allyl carbamate; cyclic ethers, such as N-tetrahydropyran and N-tetrahydrofuran; cyclic alkyl ethers, such as t-butylamide; and cyclic amines, such as N-pyrrolidinomethylamide. Exemplary amine protecting groups include, without limitation, t-butoxycarbamate, pivaloyloxymethyl carbamate, allyl carbamate, and methyl carbamate.

A particularly useful protecting group is t-butoxycarbonyl (boc). Typically, the 3-N amine group is protected by reacting the thymidine precursor with Boc$_2$O in N,N-dimethylformamide. Boc is a particularly useful amine protecting group because it reacts quickly with the amine group, does not interfere in the fluorination step, and is easily removed with hydrolysis.

The precursor is now ready for immediate [$^{18}$F]fluorination or can be stored and transported for future use. The precursor is shelf stable and is highly reactive with [$^{18}$F] fluoride in polar aprotic solvents.

Radiolabeling can be carried out using a variety of methods. In the method for preparing $^{18}$F-FLT, the precursor is treated with Kryptofix 222® and potassium carbonate in the presence of a polar aprotic solvent (Wodarski, C., et al., J. Labelled Cpd. Radiopharm., 2000, 43 1211–1218; Blocher A., et al., J. of Radioanalytical and Nuc. Chemistry, 2002, 251(1), 55–58; Martin, S. J. et al., Nuclear Medicine and Biology, 2002, 29 263–273). Useful solvents include, without limitation, acetonitrile, pyridine, N,N-dimethylformamide (DMF), dimethyl sulfoxide (DMSO), and blends thereof.

In the final step of preparing $^{18}$F-FLT, the 3-N protecting group and 5'-boc group are removed. Typically, the boc and amine protecting group are removed by hydrolyzing the radiolabeled nucleoside. Useful hydrolyzing reagents include, without limitation, acids, such as HCl, HBr, HOAc, H$_2$SO$_4$, HI, trimethylsilyliodide (TMSI), and H$_3$PO$_4$.

As should be evident from the above disclosure, the method would also be useful for preparing other radiolabeled nucleoside compounds that have a pyrimidine base. For example, the method could be used to prepare radiolabeled derivatives of uridine and cytidine. In preparing radiolabeled cytidine and uridine derivatives, the synthesis should begin with their 2'-deoxy derivatives.

EXAMPLE

Synthesis of the $^{18}$F-FLT Precursor

Step a: Synthesis of Anhydrothymidine.

To a dried round bottom flask containing thymidine(10.0 g, 41.6 mmol) was added triphenylphosphine (21.8 g, 82.2 mmol) and $CH_3CN$ (160 mL). The suspension was cooled to −20° C. ((40:60 iPrOH:$H_2O$) and dry ice). To the reaction mixture was added diisopropylazodicarboxylate (16.8 g, 82.2 mmol) as $CH_3CN$ solution (60 mL) dropwise via an addition funnel, over a period of 1 hour. After the addition, the mixture was stirred for an additional 90 minutes at 20° C. The mixture was allowed to warm to 10° C. over a period of 5 hours. The reaction was then quenched with $H_2O$ (6 mL) forming a white suspension. The reaction was allowed to stand for 30 minutes and then was filtered. The collected solid was washed with cold $CH_3CN$ and dried under vacuum to afford 7.7 g (83% yield) of a white solid. If desired, the solid may be recrystallized in EtOH.

Step b: Synthesis of 3'-β-hydroxy thymidine.

To a round bottom flask containing anhydrothymidine (3.39 g, 15 mmol) and water (20 mL) was added tetrabutylammonium hydroxide (TBAM) (30 mL, 30 mmol). The solution was allowed to stir at room temperature overnight. LC/MS indicated no anhydrothymidine was present. To the solution was added enough IRA H+ resin to neutralize all the TBAM. The resin was filtered off and washed with methanol. The filtrate was concentrated to dryness with toluene to azeotrope off the water. The residue was purified via recrystallization from acetonitrile to afford 3.1 g (85%) of a white precipitate.

Step c: Synthesis of 5'-O-Boc-3'-β-hydroxy thymidine.

To a dried round bottom flask was added 3'-β-hydroxy thymidine (242 mg, 1.0 mmol), DMF (5 mL), pyridine (355 μL, 5 mmol) and $Boc_2O$ (262 mg, 1.2 mmol). The reaction was stirred overnight at room temperature. The reaction was then poured onto water and extracted into $CH_2Cl_2$. The organics were combined, dried ($MgSO_4$), filtered, and concentrated to dryness. The residue was purified on silica gel using EtOAc as the eluent to afford 115 mg (37% yield) of a white solid. $^1$H NMR (300 MHz, $CDCl_3$) δ: 1.49 (9H, s), 1.92(3H, s), 2.21 (1H, dd, J=15.17, 2.52 Hz), 2.61–2.68 (1H, m), d, J=3.46 Hz), 3.99–4.01 (1H, m), 4.30 (1H, dd, J=11.7, 5.4 Hz), 4.36–4.38 (1H, m), 4.55 (1H, dd, J=11.7, 7.0 Hz), 6.13 (1H, d, J=8.6, 2.6 Hz), 7.67 (1H, s), 8.58 (1H, s).

Step d: Synthesis of 5'-O-Boc-3'-β-nosyl thymidine.

To a dried round bottom flask was added 5'-O-Boc-3'-β-hydroxy thymidine (500 mg, 1.46 mmol) and pyridine (7 mL). The flask was cooled to 0° C. Silver triflate (745 mg, 2.9 mmol) was added in a single portion followed by nosyl chloride (643 mg, 2.9 mmol). The reaction was stirred at 0° C. for 1 hour and then warmed to room temperature and stirred overnight. TLC (EtOAc) indicated incomplete consumption of the starting material. A second addition of silver triflate (745 mg, 2.9 mmol) was added followed by nosyl chloride (643 mg, 2.9 mmol) and the reaction was stirred for 1 hour. The mixture was poured onto water and extracted into EtOAc. The combined organic extracts were dried ($MgSO_4$), filtered, and concentrated to dryness in vacuo. The residue was purified on silica gel using 75% Hex:EtOAc as the eluent to afford 330 mg (43%) of a white solid. MS: Calc'd for $C_{21}H_{25}N_3O_{11}S$: 527.12; found: 550 (M+Na).
$^1$H NMR (300 MHz, $CD_3Cl$) δ: 1.46 (9H, s), 1.89 (3H, s), 2.41–2.44 (1H, m), (1H, m), 4.22–4.27 (2H, m), 4.39–4.43 (1H, m), 5.22 (1H, br s), 6.18–6.21 (1H, m), 737 (1H, s), 8.07–8.13 (2H, m), 8.38–8.42 (2H, m), 9.31 (1H, s).

Step e: Synthesis of 5'-O-Boc-3'-β-nosyl-2-N-Boc thymidine.

To a dried round bottom flask containing 5'-O-Boc-3'-β-nosyl thymidine (120 mg, 0.23 mmol), N,N-dimethylformamide (5 mL), and $Boc_2O$ (199 mg, 0.91 mmol) was added 4-N,N-dimethylaminopyridine (DMAP) (112 mg, 0.91 mmol). The reaction was stirred overnight at room temperature. TLC (EtOAc:Hex 1:1) indicated complete consumption of the starting material. The reaction was poured onto water and extracted into EtOAc. The combined organic extracts were dried ($MgSO_4$), filtered, and concentrated to dryness in vacuo. The residue was purified on silica gel using EtOAc:Hex 25:75 as the eluent to afford 69 mg (48%) of a white solid. MS: Calc'd for $C_{26}H_{33}N_3O_{13}S$: 627.17; found: 650.2 (M+Na). 1H NMR (300 MHz, CD3CN) δ: 1.43 (9H, s), 1.53 (9H, s), 1.93 (3H, s), 2.22 (1H, d, J=16.0 Hz), 2.72–2.76 (1(4H, m), 5.32–5.33 (1H, m), 7.37 (1H, s), 8.07–8.13 (2H, m), 8.36–8.38 (2H, m).

Many modifications and other embodiments of the invention set forth herein will come to mind to one skilled in the art to which this invention pertain having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed is:

1. A method for preparing a compound having the following formula:

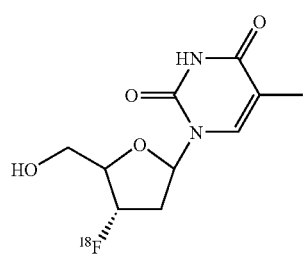

comprising:

a. [$^{18}$F]fluorinating a compound having the following formula:

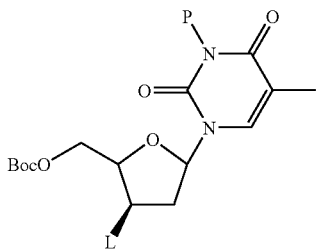

wherein P is an amine protecting group and L is a leaving group, to produce a compound having the formula:

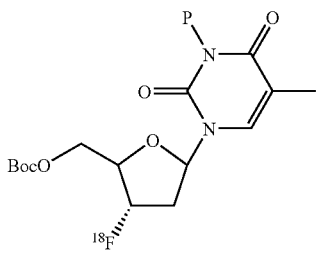

wherein P is the same as defined above; and b. removing the amine protecting group and Boc group to produce $^{18}$F-FLT.

2. A method according to claim 1, wherein P is selected from the group consisting of tert-butoxycarbamate, isopropyl carbamate, pivaloyloxymethyr, carbamate, methyl carbamate, allyl carbamate, N-tetrahydropyran, N-tetrahydrofuran; t-butylamide, and N-pyrrolidinomethylamlde.

3. A method according to claim 1, wherein P is t-butoxycarbonyl.

4. A method according to claim 1, wherein L is benzenesulfonyl, methylsulfonyt, p-methylbenzenesulfonyl, 4nitrobenzene sulfonyl, p-bromobenzenesulfonyl, trifluoromethylsulfonyl, trichloroacetimidate, 2,2,2-trifluoroethanesulfonyl, or imidazolesulfonyl.

5. A method according to claim 1, wherein L is nosylate, tosylate, or mesylate.

6. A method according to claim 1, wherein P is t-butoxycarbonyl and L is nosylate.

7. A method according to claim 1, wherein the amine protecting group and Boc groups are removed by acid hydrolysis.

8. A method according to claim 1, wherein the amine protecting group and Boc group are removed by treating the reaction product of step (a) with HCl, HBr, HOAc, $H_2SO_4$, HI, trimethylsilyllodide, or $H_3PO_4$.

* * * * *